United States Patent [19]

DeLuca et al.

[11] Patent Number: 4,851,401
[45] Date of Patent: Jul. 25, 1989

[54] NOVEL CYCLOPENTANO-VITAMIN D ANALOGS

[75] Inventors: Hector F. DeLuca, Deerfield; Heinrich K. Schnoes; Kato L. Perlman, both of Madison, all of Wis.; Andrzej Kutner, Warsaw, Poland

[73] Assignee: Wisconsin Alumni Research Foundation, Madison, Wis.

[21] Appl. No.: 219,101

[22] Filed: Jul. 14, 1988

[51] Int. Cl.$^4$ .................... C07J 9/00; A61K 31/59
[52] U.S. Cl. ............................. 514/167; 260/397.2
[58] Field of Search ..................... 260/397.2; 514/167

*Primary Examiner*—Douglas W. Robinson
*Assistant Examiner*—Joseph A. Lipovsky
*Attorney, Agent, or Firm*—Andrus, Sceales, Starke & Sawall

[57] ABSTRACT

This invention provides novel 1α-hydroxyvitamin D compounds, methods for their preparation, and pharmaceutical compositions of these compounds. The new compounds, which are characterized structurally by having a cyclopentane ring as part of their side chains, exhibit highly pronounced biological activity, both in terms of their effect on calcium metabolism and their effect on differentiating malignant cells to normal cells. By virtue of their biological properties, the new vitamin D analogs are effective as calcium-regulating, or differentiation-inducing agents, and thus find application as therapeutic agents in the treatment or prophylaxis of bone-related as well as neoplastic diseases.

11 Claims, No Drawings

NOVEL CYCLOPENTANO-VITAMIN D ANALOGS

This invention was made with United States Government support awarded by National Institutes of Health (NIH), Grant number: DK14881; AM32701. The United States Government has certain rights in this invention.

This invention relates to novel and biologically active vitamin D compounds. More specifically, this invention relates to 1α-hydroxyvitamin D analogs containing a cyclopentane ring as part of their side chains. These compounds exhibit high potency in various assays of vitamin D activity, and thus represent novel substitutes for the known vitamin D compounds.

BACKGROUND

It is well known that vitamin D is essential for proper bone growth and development and for the maintenance of blood calcium levels within the normal physiological range. It is also known that this activity of vitamin D depends on the metabolic conversion of the vitamin to its biologically active metabolites. Specifically, it has been shown that 1α,25-dihydroxyvitamin $D_3$ (1,25-$(OH)_2D_3$), the dihydroxylated metabolite normally formed from vitamin $D_3$ in the animal or human, is the active species responsible for regulating calcium transport in the intestine, and calcium resorption from bone (bone mobilization), thereby controlling the overall blood calcium level of the organism, and assuring the maintenance of calcium homeostasis. (These calcium-related activities of vitamin D metabolites or analogs will, in the following description, be referred to collectively as the "calcemic activity" of the compounds.) The discovery of the biologically active metabolites of vitamin D has stimulated the preparation of many synthetic analogs, such as, for example, 1α-hydroxyvitamin $D_3$, 1α-hydroxyvitamin $D_2$, fluorinated vitamin D derivatives, as well as analogs with altered side chains, and some of the natural, as well as several of the synthetic compounds, because of their biological potency and beneficial effects on calcium balance, have found use, or have been proposed, as therapeutic agents in the prophylaxis or treatment of various calcium metabolism and bone disorders, such as renal osteodystrophy, vitamin D-resistant rickets, osteoporosis and related diseases.

It has also been shown that 1,25-$(OH)_2D_3$ and certain related analogs, in addition to their "calcemic activity" as summarized above, also show potent activity in inhibiting the proliferation of malignant cells and inducing their differentiation to normal cells. (This activity will be referred to herein as the "differentiation activity" of vitamin D compounds.) Because of their remarkable potency as differentiation-inducing agents, 1α-hydroxyvitamin D compounds have been proposed as anticancer agents, at least for certain types of cancers (Suda et al. U.S. Pat. No. 4,391,802). More recently, a number of vitamin D side chain homologs have been disclosed, including, for example, the 24-homo-, 26-homo-, 26,27-dimethyl- and the 26,27-diethyl analogs of 1,25-$(OH)_2D_3$, which are reported to be preferentially active as differentiation-inducing agents [DeLuca et al. U.S. Pat. No. 4,717,721; Sai et al., Chem. Pharm. Bull. 33, 878 (1985); Ikekawa et al., Chem. Pharm. Bull. 35, 4362 (1987)]. In addition, 1α-hydroxyvitamin D compounds have been proposed for the treatment of certain skin disorders, such as psoriasis [Dikstein and Hartzshtark, U.S. Pat. No. 4,610,978]. This broad spectrum of activities and the varied potential uses of vitamin D compounds have further stimulated the search for novel analogs with desirable biological properties.

DISCLOSURE OF INVENTION

New vitamin D compounds have now been prepared which exhibit extremely high activity in the usual vitamin D assay systems. Specifically, these compounds are more potent than the natural metabolite, 1,25-$(OH)_2D_3$, in both their calcemic and their differentiation activities. The new compounds are 1α,25-dihydroxyvitamin D analogs containing a cyclopentane ring in the side chain, and can be represented by the following general structure:

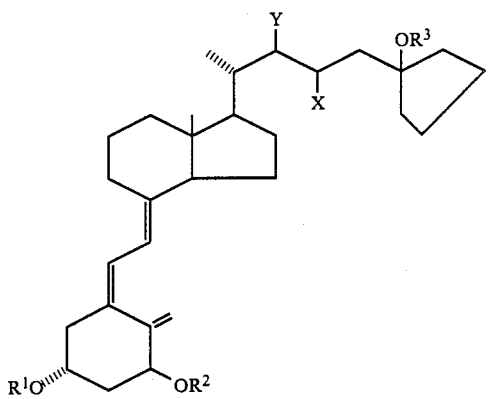

where $R^1$, $R^2$ and $R^3$ are each selected from the group consisting of hydrogen or a hydroxy-protecting group, and where X and Y both represent hydrogen, or, taken together, form a carbon-carbon bond.

This invention also provides novel synthetic intermediates, useful for the preparation of the above-shown compounds. These intermediates are characterized by the above-shown structure, where X is a phenylsulfonyl ($PhSO_2$) group, and where Y is selected from the group consisting of hydrogen, hydroxy, or protected hydroxy.

As used in this description and in the claims, a hydroxy-protecting group is any grouping used for the protection of hydroxy functions, such as, for example, acyl groups, or alkylsilyl groups, or alkoxyalkyl groups. A protected hydroxy group is any hydroxy function derivatized by one of these hydroxy-protecting groups. Examples of applicable hydroxy-protecting groups are acyl groups such as alkanoyl groups of 1 to 6 carbons, e.g. acetyl, propionyl, butyryl, etc., or benzoyl- or alkyl-, halo- or nitro-substituted benzoyl groups, alkylsilyl groups such as trimethylsilyl, triethylsilyl, dimethylethylsilyl, t-butyldimethylsilyl and analogous groupings, and alkoxyalkyl groups such as methoxymethyl, ethoxymethyl, methoxyethoxymethyl, tetrahydrofuranyl, tetrahydropyranyl, etc. The term 'alkyl' as used in this specification denotes a hydrocarbon radical of from 1 to 6 carbons in all isomeric forms.

A specific and preferred example of the novel compounds of this invention is the cyclopentano-1,25-dihydroxyvitamin $D_3$ analog, having the structure I shown below:

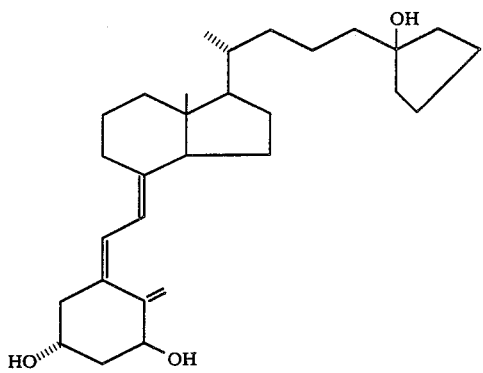

I

Another preferred example is the corresponding 22,23-dehydro analog, namely cyclopentano-1,25-dihydroxy-22-dehydrovitamin $D_3$, having the structure II as shown below:

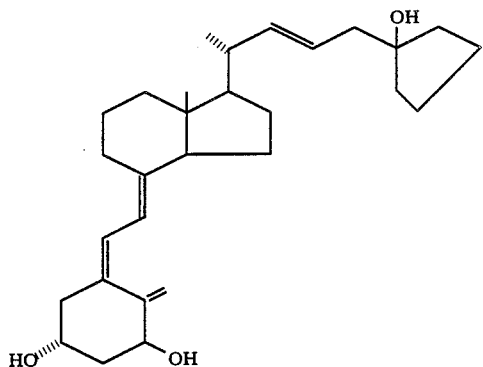

II

The above shown compounds (or their hydroxy-protected derivatives) are prepared by coupling an appropriate side chain fragment to a preformed vitamin D nucleus, possessing a suitable functional group at carbon 22. For the synthesis of the compounds of type I and II above, the appropriate vitamin D nucleus is, respectively, the 1α-hydroxyvitamin D-22-tosylate and the 1α-hydroxyvitamin D-22-aldehyde, which may be represented by the following structures.

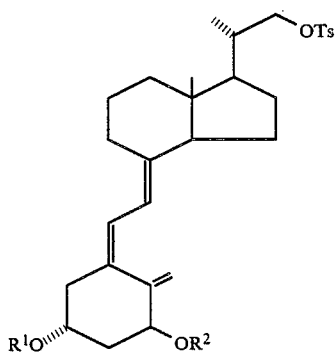

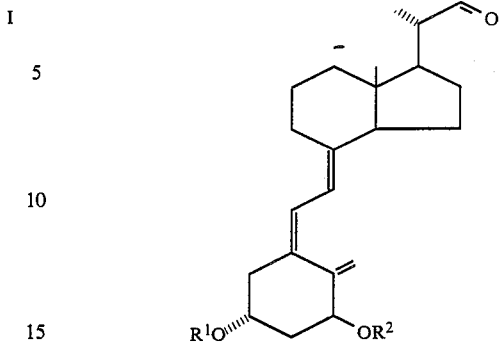

where $R^1$ and $R^2$ are hydroxy-protecting groups.

The appropriate side chain fragment is a phenylsulfonyl derivative of the following structure:

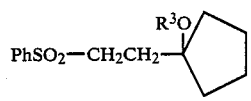

wehre $R^3$ is a hydroxy-protecting group.

Coupling of this phenylsulfonyl side chain unit with the 1α-hydroxyvitamin D-22-tosylate shown above provides in two basic steps the new vitamin D-cyclopentano analog of structure I (or hydroxy-protected derivatives thereof). Similarly, coupling of the same phenylsulfonyl side chain unit with the 1α-hydroxyvitamin D-22-aldehyde shown above, using the general conditions of Kutner et al. [Tetrahedron Letters 28, 6129 (1987)] gives the 22,23-unsaturated cyclopentano-vitamin D analog of structure II (or hydroxy-protected derivatives thereof).

The preparation fo the vitamin D-22-tosylate or 22-aldehyde starting materials is diagrammed in Scheme I (FIG. 1) [see also Kutner et al. Tetrahedron Lett. 28, 6129–6132 (1987)], whereas the prepration of the phenylsulfonyl side chain unit was achieved as outlined in Scheme II (FIG. 2). The coupling reaction between these materials to obtain the desired vitamin D side chain analogs of type I or II above is illustrated in Scheme III (FIG. 3). In the following examples, the preparation of these compounds is described in further detail. Arabic numerals (e.g. compound 1, 2, 3, etc.) designating starting materials or products, as used in these specific examples, refer to the structures so numbered in process scheme I, II and III.

Preparation of Novel Vitamin Analogs I and II General procedures

Infrared spectra (IR) were obtained on a Nicolet MX-1 FT-IR spectrometer using neat films of oily substances. Ultraviolet (UV) absorption spectra were recorded with a Hitachi Model 60-100 UV-VIS spectrometer. Nuclear magnetic resonance (NMR) spectra were recorded at 270 or 400 MHz with Bruker WH-270 or AM-400 FT spectrometers in the solvent noted. Chemical shifts (δ) are reported downfield from Me₄Si (δ0.00). Low- and high-resolution mass spectra were recorded at 70 eV (unless otherwise stated) on a Kratos MS-50 TC instrument equipped with a Kratos DS-55 Data System. High resolution data were obtained by peak matching. Samples were introduced into the ion source maintained at 120°–250° C. via a direct insertion probe.

Silica gel 60 (Merck, 70–230 or 230–400 mesh) was used for column chromatography. Thin-layer chromatography (TLC) was performed using precoated aluminum silica gel sheets with UV indicator from EM Science (Gibbstown, NJ). Solvent systems used: A: chloroform-ethanol 85:15 (v/v); B: hexane-ethyl acetate 1:1; and C: hexane-ethyl acetate 3:1. High performance liquid chromatogaphy (HPLC) was performed using a Waters Associates Liquid Chromatograph equipped with a model 6000A solvent delivery system, a Model 6 UK Universal injector and a Model 450 variable wavelength detector. Zorbax-Silica (Phenomenex) columns (6.2 mm ×20 cm and 10 mm ×25 cm) were used. Solvent systems: A: 3% 2-propanol in hexane; B: 2% 2-propanol in hexane; C: 6% 2-propanol in hexane; D: 10% 2-propanol in hexane; E: 20% 2-propanol in hexane; F: 2% ethyl acetate in hexane. Silica gel Sep-Pak (Waters Associates) cartridges were used for the prefiltration of HPLC samples.

$3\beta$-Acetoxy-22,23-bisnor-5-cholenic acid was purchased from Steraloids (Wilton, NH). Tetrahydrofuran (THF) was distilled from sodium benzophenone ketyl. Other solvents were purified by standard methods. n-Butyllithium in hexanes (Aldrich) was titrated with n-propanol in the presence of 1,10-phenantroline in THF under argon.

EXAMPLE 1

Preparation of hydroxy-protected vitamin ester (1)

Vitamin D-22-ester (1) (see Scheme I) was prepared from $3\beta$-acetoxy-22,23-bisnor-5-cholenic acid according to the general procedures described by Kutner et al. Tetrahedron Lett. 28, 6129–6132 (1987).

EXAMPLE 2

Preparation of vitamin D-22-alcohol (2) and its tosylate (3)

To a stirred solution of 136.2 mg (0.23 nmol) of ester (1) in 5 mL of anhydrous THF 25 mg (0.65 mmol) of lithium aluminum hydride was added under argon at 0° C. The suspension was stirred for 15 min at 0° C. and the excess of reagent was decomposed by the dropwise addition of 10% H$_2$O in THF. The suspension was diluted with 10 mL of THF and the stirring was continued for an additional 15 min at room temperature. The product was isolated by the standard extraction procedure with ethyl acetate. Silica gel Sep-Pak filtration in 10% ethyl acetate in hexane gave 22-alcohol (2) (118.4 mg, 91%) as a colorless oil: IR (film) 3450, 2952, 2886, 1447, 1258, 1105, 1085, 834 cm$^{-1}$; UV (EtOH) $\lambda_{max}$ 264 nm, $\lambda_{min}$ 227 nm, A264/A227=1.57; $^1$H NMR (CDCl$_3$)$\delta$0.00 (12H, s, Si—CH$_3$), 0.53 (3H, s, 18-CH$_3$), 0.85 [18H, s, Si-C(CH$_3$)$_3$], 1.04 (3H, d, J=6.4 Hz, 21-CH$_3$), 3.37 and 3.63 (1H and 1H, each m, 22-CH$_2$), 4.17 (1H, m, 3-H), 4.35 (1H, m, 1-H), 4.84 (1H, br s, 19Z-H), 5.16 (1H, br s, 19E-H), 6.00 (1H, d, J=12.2 Hz, 7-H), 6.21 (1H, d, J=12.2 Hz, 6-H); MS, m/z, 574 (M+, 17), 442 (67), 383 (11), 308 (17), 248 (100).

An ice cold solution of 42.7 mg (0.22 mmol) of p-toluenesulfonyl chloride in 50 $\mu$L of dry pyridine was added to a stirred solution of alcohol (2) at 0° C. under nitrogen. The mixture was stirred at 5° C. for 22 h and monitored by TLC (system C). The reaction mixture was poured on ice cold saturated aqueous NaHCO$_3$ and stirring was continued for another 30 min. The product was extracted with ethyl ether-hexane 1:1 (v/v). The organic phase was washed with saturated NaCl and dried over MgSO$_4$. Solvents were removed under reduced pressure and pyridine was removed in a stream of nitrogen. Crude product was purified by silica gel Sep-Pak filtration (5% ethyl acetate in hexane) to give pure tosylate (3) (54 mg, 98%): IR (film) 2950, 1580, 1367, 1267, 1189, 1178, 1099, 1085, 835 cm$^{-1}$; UV (hexane) $\lambda_{max}$ 263 nm, $\lambda_{min}$ 236 nm; $^1$H NMR (CDCl$_3$), $\delta$ 0.00 (12H, s, Si—CH$_3$), 0.43 (3H, s, 18-CH$_3$), 0.81 [18H, s, Si-C(CH$_3$)$_3$], 0.94 (3H, d, J=6.8 Hz, 2-CH$_3$), 2.40 (3H, s, Ar—CH$_3$), 3.64 and 3.91 (1H and 1H, each m, 22-CH$_2$), 4.13 (1H, m, 3-H), 4.31 (1H, m, 1-H), 4.79 (1H, brs, 19Z-H), 5.13 (1H, brs, 19E-H), 5.94 (1H, d, J=12.8 Hz, 7-H), 6.17 (1H, d, J=12.8 Hz, 6-H), 7.43 and 7.84 (2H and 2H, each m, Ar-H); MS, m/z, 728 (6), 596 (30), 556 (7), 464 (7), 424 (44), 367 (19), 292 (23), 248 (100); exact mass calcd. for C$_{41}$H$_{68}$O$_5$Si$_2$S, 728.4338; found, 728.4326.

EXAMPLE 3

Preparation of vitamin D-22-aldehyde (4)

A solution of 30 $\mu$L (0.34 mmol) of oxalyl chloride in 0.5 mL of dichloromethane was added dropwise to a stirred solution of 50 $\mu$L (0.7 mmol) of DMSO in 3 mL of dichloromethane at −60° C. under nitrogen. After the mixture was stirred for 10 min at −60° C., the solution of 27 mg (0.05 mmol) of alcohol (2) in 1 mL of dichloromethane was slowly added. The mixture was stirred at 30 min at −60° C. and 0.2 mL of triethylamine was added. The product was extracted with ethyl acetate, washed (NaCl) and dried (MgSO$_4$). Silica gel Sep-Pak filtration afforded pure (4) (17 mg, 62%) as a colorless oil: IR (film) 2954, 2929, 2884, 2857, 1727, 1472, 1375, 1256, 1085, 909, 880, 835 cm$^{-1}$; NMR (CDCl$_3$), $\delta$0.00 (12H, s, Si—CH$_3$), 0.60 (3H, s, 18-CH$_3$), 0.88 [18H, s, Si—C(CH$_3$)$_3$], 1.11 (3H, d, J=6.9 Hz, 21-CH$_3$), 4.23 (1H, m, 3-H), 4.43 (1H, m, 1-H), 4.93 (1H, br s, 19Z-H), 5.19 (1H, br s, 19E-H), 6.07 (1H, d, J=10.0 Hz, 7-H), 6.26 (1H, d, J=10.0 Hz, 6-H), 9.54 (1H, d, J=3 Hz, 22-H); UV (hexane) $\lambda_{max}$ 264 nm, $\lambda_{min}$ 227 nm, A264/A227 =1.9; MS, m/z, 572 (M+, 13), 440 (53), 383 (11), 308 (14), 248 (100); exact mass calculated for C$_{34}$H$_{60}$O$_3$Si$_2$, 572.4081; found, 572.4117.

An improved yield of aldehyde (4) was obtained when the above oxidation procedure was conducted under the following conditions: A solution of 15 $\mu$L (0.17 mmol) of oxalyl chloride in 0.75 mL anhydrous dichloromethane was added dropwise to a stirred solution of 25 $\mu$L (0.36 mmol) dimethylsulfoxide in 0.25 mL anhydrous dichloromethane at −60° C. under an argon atmosphere. After the mixture was stirred for 10 min at −60° C., a solution of 20.3 mg (0.035 mmol) of alcohol (2) in 0.5 ml of anhydrous dichloromethane was added slowly, and the flask was rinsed with an additional 0.2 mL of the same solvent. The resulting mixture was stirred for 30 min at −60° C. and 0.3 mL (2.15 mmol) of triethylamine was added (−60° C.). The mixture was stirred for 5 min, warmed to 0° C. and extracted with ether. The ether phase was washed with brine and dried (MgSO$_4$), silica gel Sep-Pak filtration afforded (4) as a colorless oil which was further purified by HPLC (Zorbax-Sil 0.94×25 cm, 10% ethyl acetate in hexane) to give pure aldehyde (4) (19 mg, 96% yield); only a trace of alcohol starting material was recovered (0.12 mg).

EXAMPLE 4

Preparation of the phenylsulfonyl side chain fragment (10)

The hydroxy-protected side chain fragment was prepared from $\beta$-propiolactone (5) as starting material. The lactone (5) was converted to the diol (6) by reaction with 1,4-bis (bromomagnesium)butane according to a known method [P. Canonne, et al. J. Org. Chem. 45, 1828 (1980)]. The further conversion of compound (6) to the desired side chain unit (10) was done according to the general methods reported by Kutner et al., Tetrahedron Lett. 28, 6129 (1987). Thus, the primary alcohol function in diol (6) was converted to the tosylate (7) and the tosylate displaced by thiophenol anion to yield the phenylsulfide derivative (8). After oxidation of the latter with m-chloroperbenzoic acid, the corresponding phenylsulfone (compound 9) was obtained, which was converted to the desired hydroxy-protected form by conversion (using an excess of triethylsilyl chloride and imidazole in dimethylformamide, at room temperature for ca. 2 hours) to the triethylsilyl derivative, compound (10). Protected sulfone (10) was obtained in 48% overall yield as a thick colorless oil: IR (film) 3050, 2900, 1440, 1405, 1300, 1230, 1045, 1000 cm$^{-1}$; $^1$H NMR (CDCl$_3$), $\delta$0.47 (6H, J=5.7 Hz, Si—CH$_2$), 0.86 (9H, t, J=5.7 Hz, CH$_3$), 1.46-1.57 (4H, m), 1.63-1.71 (4H, m), 1.86-1.89 (2H, m), 3.23-3.26 (2H, m), 7.58 (2H, t, J=7.3 Hz, Ar—H, meta), 7.66 (1H, t, J=7.3 Hz, Ar—H, para), 7.92 (2H, d, J=7.3 Hz, Ar—H, ortho); MS, m/z (30 eV, rel. int.), 368 (M+, 0.01), 339 (M+-Et, 100), 227 (8), 199 (8), 163 (17), 135 (10), 115 (9), 95 (13), 87 (12), 75 (14); exact mass calcd. for C$_{19}$H$_{32}$O$_3$SSi, 368.1841; found, 368.1936.

EXAMPLE 5

Preparation of cyclopentano-1,25-dihydroxyvitamin D$_3$ analog I

Dissopropylamine (8 $\mu$L) was added to a stirred solution of n-BuLi (41 $\mu$L; 1.35 M in hexane) containing 1.10 phenanthroline as an indicator at $-78°$ C. under argon. After stirring under argon for 30 min, a solution of the phenylsulfone derivative (28 mg) (10) in THF (200 $\mu$L) was added. After stirring the resulting brown mixture at $-75°$ C. under argon for 30 min, the cooling bath was replaced by a CCl$_4$/dry ice bath. After 15 min of stirring at $-21°$ C., a THF-solution of tosylate (11 mg) (3) was added as the color of the reaction mixture turned back to red. The solution was stirred at $-20$ to $-10°$ C. for 3.5 h; then saturated NH$_4$Cl was added at $-10°$ C. and the mixture was extracted with hexane. The organic phase was washed with saturated NaCl solution and then filtered through a silica gel Sep-Pak cartridge, to provide the intermediary sulfone derivative (11) as a mixture of C-23 epimers. This product was directly desulfonylated with 5% sodium amalgam. A saturated solution of Na$_2$HPO$_4$ in methanol (500 $\mu$L), was added to a stirred solution of the sulfone derivative (11) in anhydrous THF (500 $\mu$L), followed by addition of more powdered NaHPO$_4$. The mixture was stirred under argon for 30 min and cooled to 0° C. Fresh 5% sodium amalgam was then added and stirring continued for 3 h at 5° C. The progress of the reaction was monitored by TLC (system C), and when complete, the mixture was diluted with hexane and stirred for nother 15 min. The hexane layer was decanted and the methanol layer was washed with several portions of hexane. The combined hexane extracts were washed with ice cold saturated NaCl solution, and then filtered through a silica gel Sep-Pak cartridge to give hydroxy-protected triol (105 $\mu$g) (12). The protecting groups were removed by treatment of a THF solution (500 $\mu$L) of (12) with a solution of tetrabutylammonium fluoride in THF (10 $\mu$L; 1 M solution). After stirring for 50 min at 50° C. under argon, ether was added and the organic phase was washed with NaCl solution. Solvent was then evaporated and the residue was isolated by filtration through a silica gel Sep-Pak cartridge (10% 2-propanol in hexane), and the product, the desired vitamin analog I, was then purified by preparative HPLC (10 mm $\times$25 cm column, system D). Triol I (54 $\mu$g), obtained in 12% yield (from 3), exhibited the following physical properties: IR (film) 3360, 2930, 1605, 1442, 1378, 1291, 1145, 1105, 1080, 1062 cm$^{-1}$; UV (10% 2-propanol in hexane) $\lambda_{max}$ 264 nm, $\lambda_{min}$ 228 nm, A264/A228=1.71; $^1$H NMR (CD$_3$OD), $\delta$0.48 (3H, s, 18CH$_3$), 0.87 (3H, d, J=6.4 Hz, 21-CH$_3$), 4.03 (1H, m, 3-H), 4.25 (1H, m, 1-H), 4.80 (1H, br s, 19Z-H), 5.19 (1H, br s, 19E-H), 5.98 (1H, d, J=11.2 Hz, 7-H), 6.23 (1H, d, J=11.1 Hz, 6-H); MS, m/z (relative intensity), 442 (M+, 5), 424 (43), 406 (38), 388 (7), 373 (7), 298 (6), 285 (12), 269 (20), 251 (24), 134 (100), 85 (28); exact mass calcd. for C$_{29}$H$_{48}$O$_3$, 442.3447; found, 442.3438.

EXAMPLE 6

Preparation of the cyclopentano-1,25-dihydroxy-22-dehydrovitamin D$_3$ analog II To a stirred solution of 27 mg (73 $\mu$mol) 1-[-(phenylsulfonyl)ethyl]-1-[(triethylsilyl)oxy]-cyclopentane (10) in 300 $\mu$L anhydrous tetrahydrofuran (containing 1,10-phenanthroline as indicator) was added under argon atmosphere at $-78°$ C., 11 $\mu$L diisopropylamine (80 $\mu$mol) followed by 62 $\mu$L n-BuLi (1.3 M in hexane) 80 $\mu$mol). The solution was stirred under argon atmosphere at $-78°$ C. for 30 min, then 1.8 mg aldehyde (4) (3 $\mu$mol) in 300 $\mu$L anhydrous tetrahydrofuran was added and stirred at $-78°$ C. for 1 h. The mixture was decomposed by the addition of 1 mL of saturated NH$_4$Cl solution warmed to 0° C. and extracted with ethyl acetate. The ethyl acetate was washed with brine and water, dried over anhydrous MgSO$_4$, filtered and evaporated. Preparative HPLC (Zorbax-Sil 9.4 mm $\times$25 cm column, solvent system, 10% ethyl acetate in hexane) gave 0.5 mg unreacted aldehyde and 2.3 mg of hydroxysulfones (13) as a mixture of epimers.

A saturated solution of Na$_2$HPO$_4$ in methanol (1.0 mL) was added to a stirred solution of hydroxysulfones (13) (2.3 mg) in 1.0 mL of anhydrous THF followed by powdered anhydrous Na$_2$HPO$_4$ (160 mg). The mixture was stirred under argon atmosphere for 30 min and cooled to 0° C. Fresh 5% sodium amalgam (ca. 400 mg) was then added, and the mixture was stirred for 16 h at 5° C. The mixture was diluted with 5 mL of hexane and stirring was continued for 15 min. Solvents were decanted and the solid material was washed with hexane (3 $\times$5 mL). Ice and brine were added to the combined organic solution. The organic layer was separated and passed through a Sep Pak cartridge in hexane. HPLC purification gave 260 $\mu$g of compound 14 together with 126 $\mu$g of 22-hydroxylated product (Zorbax-Sil 9.4 mm $\times$25 cm column, 10% ethyl acetate in hexane). The protected triol (14) was dissolved in 1.0 mL of anhydrous THF and tetrabutylammonium fluoride in anhydrous THF (50 $\mu$L, 1 M solution) added. The mixture was stirred under argon atmosphere for 1 h at 50° C. Ether (5 mL) was then added and the organic phase was washed with brine. Solvents were removed and the residue was dissolved in 1:1 2-propanol/hexane and passed through a silica Sep Pak cartridge. Preparative HPLC (Zorbax-Sil 9.4 mm $\times$25 cm column, 20% 2-propanol in hexane) gave the 22E-dehydro-triol (II) (110 $\mu$g) UV (EtOH) $\lambda_{max}$ 264 nm, $\lambda_{min}$ 228, A26-

4/A228=1.7; $^1$H NMR (CDCl$_3$) $\mu$0.56 (3H, s, 18-CH$_3$), 1.04 (3H, d, J=6.5 Hz, 21-CH$_3$), 4.23 (1H, m, 3-H), 4.44 (1H, m, 1-H), 4.99 (1H, br s, 19Z-H), 5.32 (1H, br s, 19E-H), 5.41 (2H, m, 22 and 23 H), 6.01 (1H, d, J=11.3 Hz, 7-H), 6.37 (1H, d, J=11.2 Hz, 6-H). MS, m/z (relative intensity) 440 (M$^+$, 14), 422 (51), 404 (20), 287 (10), 269 (22), 251 (18), 152 (30), 134 (100), 116 (8) 85 (98); exact mass calcd. for C$_{29}$H$_{44}$O$_3$, 440.3290; found, 440.3305.

Biological Activity of the New Vitamin D Analogs

The new vitamin D analogs, cyclopentano-1,25-dihydroxy-vitamin D$_3$ (compound I) and cyclopentano-1,25-dihydroxy-22E-dehydro-vitamin D$_3$ (compound II) were assayed for both calcemic activity and differentiation activity, using established procedures known in the art. The assay procedures and results obtained are described in the following examples.

EXAMPLE 7

Intestinal calcium transport activity and bone calcium mobilization activity of compounds I and II Male weanling rats (obtained from Harlan-Sprague Dawley Co., Madison, WI) were fed a low calcium, vitamin D-deficient diet (0.02% Ca, 0.3% P) as described by Suda et al. (J. Nutr. 100, 1049-1052, 1970), for a total of 4 weeks ad libitum. At the end of the third week, the animals were divided randomly into groups of 6 rats each. One group (the control group) received a daily dose of solvent vehicle (0.1 mL of 95% propylene glycol/5% ethanol) by interperitoneal (i.p.) injection for a total of 7 days. The other groups received the amounts of test compound (i.e. 1,25-(OH)$_2$D$_3$, compound I, or compound II) as indicated in Table 1, dissolved in the same amount of solvent vehicle by daily injection over a period of 7 days. The animals were killed 24 hours after the last injection, their intestines were removed for intestinal calcium transport measurements, and their blood was collected for the assay of bone calcium mobilization (measurement of serum calcium levels). Intestinal calcium transport was measured by the everted gut sac technique [Martin & DeLuca, Am. J. Physiol. 216, 1351 (1969)] as described by Halloran and DeLuca [Arch. Biochem. Biophys. 208, 477-486 (1981)]. The results, expressed in the usual fashion as a ratio of serosal/mucosal calcium concentrations, are given in Table 1 below. Bone calcium mobilization was assayed by measuring serum calcium levels, using the standard procedures: 0.1 mL aliquots of serum were diluted with 1.9 mL of a 0.1% aqueous solution of LaCl$_3$ and calcium concentrations were then determined directly by atomic absorption spectroscopy. Results, expressed as mg % calcium, are also presented in Table 1 below.

TABLE 1

Intestinal Calcium Transport and Bone Calcium Mobilization (Serum Calcium Levels) Activity of the Cyclopentano-Vitamin D Analogs

| Compound Administered | Amount ng/day | Ca Transport [Ca serosal]/[Ca mucosal] mean ± S.E.M. | Serum Calcium mg % mean ± S.E.M. |
|---|---|---|---|
| none (control) | 0 | 2.4 ± 0.22 | 3.7 ± 0.06 |
| 1,25-(OH)$_2$D$_3$ | 50 | 8.3 ± 0.43 | 4.6 ± 0.10 |
| Cyclopentano-1,25-(OH)$_2$D$_3$ (Compound I) | 25 | 7.7 ± 0.37 | 5.5 ± 0.31 |
| | 125 | 10.4 ± 0.10 | 7.4 ± 0.06 |
| Cyclopentano-1,25-(OH)$_2$-22-dehydro-D$_3$ (Compound II) | 50 | 8.3 ± 0.81 | 5.9 ± 0.14 |

EXAMPLE 8

Differentiation activity of Compounds I and II

Degree of differentiation of HL-60 cells (human leukemia cells) in response to test compounds was assessed by three different assays: NBT reduction, esterase activity, and phagocytosis activity. The NBT reduction and phagocytosis assays were carried out as described by DeLuca et al. in U.S. Pat. No. 4,717,721. The third assay, measuring nonspecific acid esterase as a marker for degree of differentiation was conducted according to the method given in Sigma Kit. No. 90, available from Sigma Chemical Corp., St. Louis, MO [see also, Ostrem et al., Proc. Natl. Acad. Sci. USA 84, 2610 (1987); Ostrem et al., J. Biol. Chem. 262, 14164 (1987)]. Results are shown in Table 2 below. The data for the three assays are presented as the percent of differentiated cells resulting from treatment with various concentrations of 1,25-(OH)$_2$D$_3$ (used as comparison standard) or the cyclopentano-vitamin D analogs I and II.

TABLE 2

Differentiation Activity of Cyclopentano-1,25-(OH)$_2$D$_3$ (Compound I) and Cyclopentano-1,25-(OH)$_2$-22-dehydro-D$_3$ (Compound II) in HL-60 Cell Cultures

| Compound Administered | Concentration (molar) | % Differentiated Cells | | |
|---|---|---|---|---|
| | | NBT | Esterase | Phagocytosis |
| 1,25-(OH)$_2$D$_3$ | $1 \times 10^{-7}$ | 89 ± 3 | 93 ± 2 | 88 ± 3 |
| | $1 \times 10^{-8}$ | 58 ± 4 | 63 ± 4 | 59 ± 3 |
| | $1 \times 10^{-9}$ | 34 ± 3 | 37 ± 3 | 34 ± 2 |
| Cyclopentano-1,25-(OH)$_2$D$_3$ (Compound I) | $5 \times 10^{-8}$ | 90 ± 4 | 88 ± 4 | 86 ± 3 |
| | $1 \times 10^{-8}$ | 81 ± 3 | 80 ± 4 | 82 ± 4 |
| | $5 \times 10^{-9}$ | 63 ± 2 | 66 ± 4 | 65 ± 4 |
| | $1 \times 10^{-9}$ | 46 ± 2 | 45 ± 3 | 45 ± 3 |
| Cyclopentano 1,25-(OH)$_2$-22-dehydro-D$_3$ (Compound II) | $1 \times 10^{-7}$ | 95 ± 3 | 95 ± 3 | 92 ± 6 |
| | $5 \times 10^{-8}$ | 90 ± 3 | 91 ± 2 | 89 ± 3 |
| | $1 \times 10^{-8}$ | 80 ± 3 | 76 ± 4 | 78 ± 4 |
| | $5 \times 10^{-9}$ | 63 ± 2 | 67 ± 4 | 63 ± 3 |
| | $1 \times 10^{-9}$ | 47 ± 3 | 45 ± 2 | 49 ± 3 |
| | $5 \times 10^{-10}$ | 39 ± 3 | 39 ± 3 | 40 ± 3 |

The preceding test results establish that the new cyclopentano analogs I and II, possess high calcemic and differentiation activity. Indeed, the assay results listed in Table 1 and Table 2 show that, with respect to calcemic activity and differentiation activity, the two cyclopentano vitamin D analogs are more potent than the natural hormone, 1,25-(OH)$_2$D$_3$. Thus, the calcium transport response elicited by analogs I and II (see Table 1) is approximately the same as that given by 1,25-(OH)$_2$D$_3$, but the two analogs are distinctly more potent than 1,25-(OH)$_2$D$_3$ in their effect on calcium mobilization from bone (Table 1). Similarly, the data in Table 2 show that analogs I and II are approximately five times more active than 1,25-(OH)$_2$D$_3$ in inducing the differentiation of leukemic cells. This is evident, for example, from the entries showing that both compounds I and II achieve 90% differentiation at a concentration of $5 \times 10^{-8}$ M, whereas a five-fold higher concentration ($1 \times 10^{-7}$ M)

of 1,25-(OH)₂D₃ is required to produce the same degree of differentiation.

Based on these results, one can conclude that both of the new cyclopentano analogs can be used effectively as calcium regulating agents or as differentiation-inducing agents. Thus, the new analogs can be employed in the prophylaxis or treatment of calcium metabolism disorders such as renal osteodystrophy, vitamin D-resistant rickets, osteoporosis and related diseases. Likewise, their high potency in inducing the differentiation of malignant cells to normal cells indicates that the cyclopentano analogs can be used in place of such known compounds as 1,25-(OH)₂D₃ for the treatment of neoplastic disease, especially leukemias.

For treatment purposes, these compounds may be formulated as solutions in innocuous solvents, or as emulsions, suspensions, or dispersions in suitable and innocuous solvents and carriers, or as pills, tablets, or capsules by conventional methods known in the art. Such formulations may also contain other pharmaceutically-acceptable excipients, such as inert carriers, or stabilizers, anti-oxidants, binders, coloring agents or emulsifying or taste-modifying agents.

The compounds are advantageously administered by injection, or by intravenous infusion of suitable sterile solutions, or in the form of oral doses as pills, tablets, or capsules. For the treatment or prophylaxis of calcium metabolism disorders, the compounds are administered to subjects in dosages sufficient to correct or prevent the disorder. Suitable dosage ranges are from 0.1 to 10 μg per day, depending on the condition to be treated and the response of the subject. Similar dosage amounts are appropriate in using the novel compounds of this invention for the treatment of neoplastic diseases.

We claim:

1. Compounds having the structure:

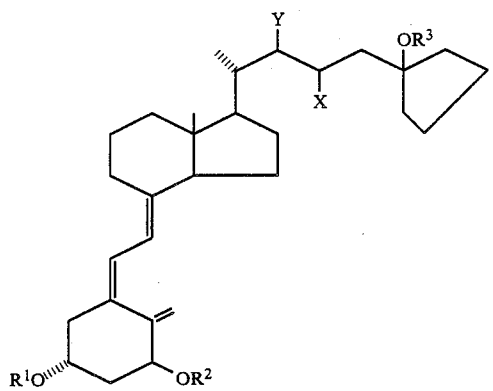

wherein R¹, R², and R³, which may be the same or different, are each selected from the group consisting of hydrogen and a hydroxy-protecting group, X is selected from the group consisting of hydrogen and phenylsulfonyl, Y is selected from the group consisting of hydrogen, hydroxy and protected hydroxy, and where X and Y, taken together, form a carbon-carbon bond.

2. The compounds as claimed in claim 1, where the hydroxy-protecting group is an acyl group, or an alkoxyalkyl group.

3. The compounds as claimed in claim 1, where the hydroxy-protecting group is an alkylsilyl group.

4. A pharmaceutical composition containing at least one of the compounds as claimed in claim 1 together with a pharmaceutically-acceptable excipient.

5. A pharmaceutical composition as claimed in claim 4, in which the compounds, alone or in combination, are present in an amount from about 0.1 to about 10 μg.

6. The compound having the structure:

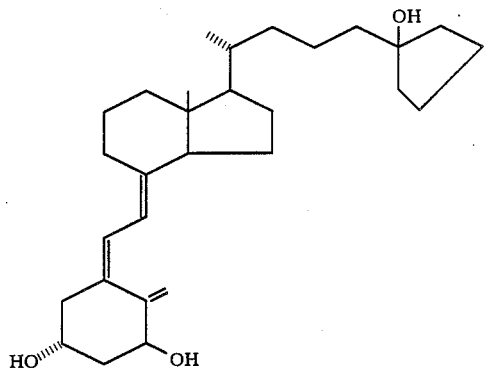

7. A pharmaceutical composition containing the compound of claim 6 together with a pharmaceutically-acceptable excipient.

8. A pharmaceutical composition as claimed in claim 7, in which the compound is present in an amount from about 0.1 to about 10 μg.

9. The compound having the structure:

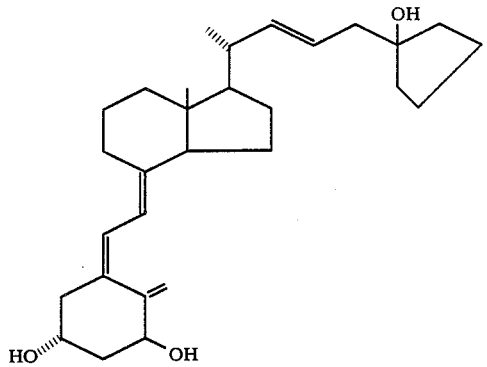

10. A pharmaceutical composition containing the compound of claim 9, together with a pharmaceutically-acceptable excipient.

11. A pharmaceutical composition as claimed in claim 10, in which the compound is present in an amount from about 0.1 to about 10 μg.

* * * * *